(12) United States Patent
Sharifi-Mehr et al.

(10) Patent No.: US 12,059,180 B2
(45) Date of Patent: Aug. 13, 2024

(54) POLYAXIAL SCREWDRIVER FOR A PEDICLE SCREW SYSTEM

(71) Applicant: Stryker European Operations Holdings LLC, Kalamazoo, MI (US)

(72) Inventors: Amir Ali Sharifi-Mehr, Bloomingdale, NJ (US); Ernie Corrao, Bethel, CT (US); Andy Wonyong Choi, Irvine, CA (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 205 days.

(21) Appl. No.: 17/863,815

(22) Filed: Jul. 13, 2022

(65) Prior Publication Data
US 2023/0000532 A1 Jan. 5, 2023

Related U.S. Application Data

(60) Division of application No. 16/828,239, filed on Mar. 24, 2020, now Pat. No. 11,389,211, which is a
(Continued)

(51) Int. Cl.
*A61B 17/70* (2006.01)
*A61B 17/86* (2006.01)
(Continued)

(52) U.S. Cl.
CPC ...... *A61B 17/7082* (2013.01); *A61B 17/7032* (2013.01); *A61B 17/7035* (2013.01);
(Continued)

(58) Field of Classification Search
CPC ............ A61B 17/7082; A61B 17/7035; A61B 17/888; A61B 17/8615; F16B 23/003; B25B 13/10; B25B 15/005
See application file for complete search history.

(56) References Cited

U.S. PATENT DOCUMENTS 2,248,695 A 7/1941 Bradshaw
3,498,174 A 3/1970 Schuster et al.
(Continued)

FOREIGN PATENT DOCUMENTS

EP 1222899 A2 7/2002
EP 1293168 A2 3/2003

OTHER PUBLICATIONS

Communication from EP 08 100 656, dated Jun. 4, 2010.
European Search Report, EP 08 10 0656, dated May 9, 2008.
European Search Report, EP 10162029, dated May 26, 2010.

*Primary Examiner* — David W Bates
(74) *Attorney, Agent, or Firm* — Lerner David LLP (57) ABSTRACT

A polyaxial screwdriver for inserting a bone screw in a vertebra. A polyaxial bone screw assembly includes a coupling element. When a screw engaging end of the polyaxial screwdriver is lowered on the head of the bone screw, the complimentary surfaces of the screw engaging end of the screwdriver and the head of the screw self-align. A ratchet mechanism formed in the screwdriver provides progressive and automatic locking of the polyaxial screwdriver to the coupling element and prevents the accidental unthreading from the coupling element. In another embodiment of the polyaxial screwdriver, a collet slides over the outside surface of the upper end of the coupling element and locks on to the coupling element. In yet another embodiment of a polyaxial screwdriver, the outer sleeve of the polyaxial screwdriver has a split end that securely engages the coupling element.

20 Claims, 10 Drawing Sheets

Related U.S. Application Data continuation of application No. 15/583,200, filed on May 1, 2017, now Pat. No. 10,639,080, which is a division of application No. 14/661,337, filed on Mar. 18, 2015, now Pat. No. 9,649,139, which is a continuation of application No. 13/536,265, filed on Jun. 28, 2012, now Pat. No. 8,998,921, which is a continuation of application No. 12/008,982, filed on Jan. 15, 2008, now Pat. No. 8,231,635.

(60) Provisional application No. 60/881,106, filed on Jan. 18, 2007.

(51) Int. Cl.
*A61B 17/88* (2006.01)
*A61B 17/56* (2006.01)

(52) U.S. Cl.
CPC ...... *A61B 17/7037* (2013.01); *A61B 17/8605* (2013.01); *A61B 17/8888* (2013.01); *A61B 2017/564* (2013.01)

(56) References Cited

U.S. PATENT DOCUMENTS

| | | | |
|---|---|---|---|
| 3,584,667 | A | 6/1971 | Reiland |
| 3,693,495 | A | 9/1972 | Wagner |
| 3,763,725 | A | 10/1973 | Reiland |
| 3,812,757 | A | 5/1974 | Reiland |
| 3,908,489 | A | 9/1975 | Yamamoto et al. |
| 4,006,660 | A | 2/1977 | Yamamoto et al. |
| 4,197,889 | A | 4/1980 | Peterson |
| 4,267,870 | A | 5/1981 | Warner |
| 4,502,825 | A | 3/1985 | Yamada |
| 4,504,180 | A | 3/1985 | Ishii et al. |
| 5,171,117 | A | 12/1992 | Seidl |
| 5,207,132 | A | 5/1993 | Goss et al. |
| 5,423,819 | A | 6/1995 | Small et al. |
| 5,553,983 | A | 9/1996 | Shinjo |
| 5,649,931 | A | 7/1997 | Bryant et al. |
| 5,697,743 | A | 12/1997 | Parker |
| 5,836,430 | A * | 11/1998 | Vasudeva ............... F16D 41/18 81/63.1 |
| 5,946,988 | A | 9/1999 | Metz-Stavenhagen |
| 6,158,310 | A | 12/2000 | Goss et al. |
| 6,224,596 | B1 | 5/2001 | Jackson |
| 6,321,623 | B1 | 11/2001 | Dykes et al. |
| 6,328,512 | B1 | 12/2001 | Miranda |
| 6,488,681 | B2 | 12/2002 | Martin et al. |
| 6,540,460 | B2 | 4/2003 | Miranda et al. |
| 6,554,834 | B1 | 4/2003 | Crozet et al. |
| 7,311,022 | B2 | 12/2007 | Putney et al. |
| 8,162,988 | B2 | 4/2012 | Delecrin et al. |
| 8,460,307 | B2 | 6/2013 | Saidha et al. |
| 8,845,652 | B2 * | 9/2014 | Heinz ............... B25B 23/101 606/104 |
| 8,955,417 | B2 | 2/2015 | Stiebitz et al. |
| 8,998,960 | B2 | 4/2015 | Jackson |
| 9,821,442 | B2 | 11/2017 | Campbell |
| 9,867,639 | B2 | 1/2018 | Biedermann et al. |
| 10,335,198 | B2 | 7/2019 | Biedermann et al. |
| 10,385,902 | B2 | 8/2019 | Wunderlich et al. |
| D883,765 | S | 5/2020 | Schwartzkopf |
| 10,788,077 | B2 | 9/2020 | Goss |
| 11,058,469 | B2 | 7/2021 | Mahajan et al. |
| 2002/0072750 | A1 | 6/2002 | Jackson |
| 2002/0091386 | A1 * | 7/2002 | Martin ............... A61B 17/7037 606/278 |
| 2004/0138662 | A1 | 7/2004 | Landry et al. |
| 2005/0098000 | A1 | 5/2005 | Brooks |
| 2005/0267477 | A1 | 12/2005 | Jackson |
| 2006/0036244 | A1 | 2/2006 | Spitler et al. |
| 2006/0069391 | A1 | 3/2006 | Jackson |
| 2006/0089644 | A1 | 4/2006 | Felix |
| 2006/0111712 | A1 | 5/2006 | Jackson |
| 2006/0111715 | A1 * | 5/2006 | Jackson ............ A61B 17/7032 606/279 |
| 2006/0278049 | A1 | 12/2006 | Baynham |
| 2006/0293677 | A1 | 12/2006 | Oepen |
| 2007/0288026 | A1 | 12/2007 | Shluzas |
| 2008/0045970 | A1 * | 2/2008 | Saidha ............... A61B 17/7035 81/436 |
| 2009/0129887 | A1 | 5/2009 | Chang |
| 2009/0175702 | A1 | 7/2009 | Lin |
| 2009/0264895 | A1 | 10/2009 | Gasperut et al. |
| 2013/0131737 | A1 | 5/2013 | Cheng et al. |

* cited by examiner

POLYAXIAL SCREWDRIVER FOR A PEDICLE SCREW SYSTEM

CROSS-REFERENCE TO RELATED APPLICATIONS

The present application is a divisional of U.S. patent application Ser. No. 16/828,239, filed on Mar. 24, 2020, which is a continuation of U.S. patent application Ser. No. 15/583,200, filed on May 1, 2017, which is a divisional of U.S. patent application Ser. No. 14/661,337, filed on Mar. 18, 2015, which is a continuation of U.S. patent application Ser. No. 13/536,265, filed on Jun. 28, 2012 which, in turn, is a continuation of U.S. patent application Ser. No. 12/008,982, filed on Jan. 15, 2008, which claims the benefit of the filing date of U.S. Provisional Patent Application No. 60/881,106 filed Jan. 18, 2007, the disclosures of which are hereby incorporated herein by reference.

FIELD OF THE INVENTION

The present invention relates generally to spinal fixation devices and more specifically relates to a pedicle screw system having an improved screwdriver coupling interface and securing of the screwdriver to the polyaxial screw assembly.

DESCRIPTION OF THE RELATED ART

The spinal column is a highly complex system of bones and connective tissues that provides support for the body and protects the delicate spinal cord and nerves. There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

A technique commonly referred to as spinal fixation is employed for fusing together and/or mechanically immobilizing vertebrae of the spine. Spinal fixation may also be used to alter the alignment of adjacent vertebrae relative to one another so as to change the overall alignment of the spine. Such techniques have been used effectively to treat the above-described conditions and, in most cases, to relieve pain suffered by the patient. Spinal fixation often involves use of polyaxial pedicle screws fixed to the vertebrae. However, there are some disadvantages associated with current pedicle screws and polyaxial screwdrivers used to install them. There remains room for improvement in the manner of engaging the screw head, the complexity of use, the required manipulation of the many parts associated with some complex devices and improved screw loading during installation.

SUMMARY OF THE INVENTION

A screw having a head which includes a central projection on the upper portion, preferably a spherical underside and a plurality of projections extending from an upper surface of the head is disclosed. In one embodiment, the projections are arranged about the periphery of the head, preferably, the projections or at least a portion of them are connected by a web of material.

Formatting with a screw head of the type described above, a driver in accordance with the present invention may have an end which mates with the structure of the screw head. It need not match or mate precisely, but instead may have structure to mate with a portion of the structure of the screw head. The driver may include a transverse stabilization structure. The driver may include a structure for locking the driver to the screw or a polyaxial screw coupling element.

The present invention may include a polyaxial screwdriver having a handle and a screw engaging end. The screw engaging end engages the head of a polyaxial screw such that when the screwdriver is rotated via the handle, the polyaxial screw is advanced or retracted in the vertebra. The polyaxial screwdriver has an internal shaft and an outside sleeve slidably inserted over the internal shaft. The screw engaging end has semi-cylindrical cutouts that are spaced at a distance from each other. Placed between the semi-cylindrical cutouts are cylindrical structures.

The present invention may also include a polyaxial bone screw assembly having a bone screw. The polyaxial bone screw assembly also includes a coupling element. The coupling element has a bore for receiving the bone screw. The bone screw has a head that has a flat surface. A cylindrical wall is formed on the flat surface. Solid cylinders are formed on the outside surface of the cylindrical wall. The solid cylinders are located on the head such that they can align with the semi-cylindrical cutouts when the screw engaging end of the screwdriver is placed on top of the head. When the screw engaging end is lowered on the head, the semi-cylindrical cutouts would slide on top of the cylindrical structures and thereby self-align.

As the screw engaging end is lowered in the coupling element, threads formed on the shaft of the screw driver would align with threads in the coupling element. Rotation of sleeve would results in engagement of these two threads. The precise mating of the screw engaging end and head along with the engagement of these threads results in secure attachment of the screwdriver to the screw. A ratchet mechanism formed in the screwdriver provides progressive and automatic locking of the polyaxial screwdriver to the coupling element and prevents the accidental unthreading from the coupling element. When the screwdriver is used to unscrew, a button is pressed to disengage the ratchet from gear teeth and thereby allow the sleeve to be rotated in reverse direction to remove the screw.

In another embodiment of the polyaxial screwdriver, the outer sleeve of the polyaxial screwdriver has a collet formed at the end that is near the screw engaging end. Projections are formed on the internal surface of the collet. The end of the sleeve that is closer to the handle has external threads formed on it. A nut is located above the external threads. The nut has internal threads that are adapted to threadably engage the external threads. When the polyaxial screwdriver is lowered on the head, collet slides over the outside surface of the upper end of the coupling element and locks on to the coupling element. Next, the nut is threaded on to the external threads to securely fasten the screwdriver to the polyaxial bone screw assembly.

In yet another embodiment of a polyaxial screwdriver, the outer sleeve of the polyaxial screwdriver has a split end. The split end securely engages the coupling element. A short ring is located around the split end of outer sleeve. The short ring when pulled towards the handle would engage ramps formed on the external surfaces of the split end thereby moving split ends towards the center of the sleeve and allowing them to disengage from the coupling element.

The present invention also resides in the ornamental appearance of the polyaxial screw as shown in FIGS. 2, 4, 5, 7, 9, 10 and 11. The present invention also resides in the ornamental appearance of the polyaxial screwdriver as shown in FIGS. 1, 2, 3, 7, 8, 9, 10 and 11.

DETAILED DESCRIPTION

Figure 1:
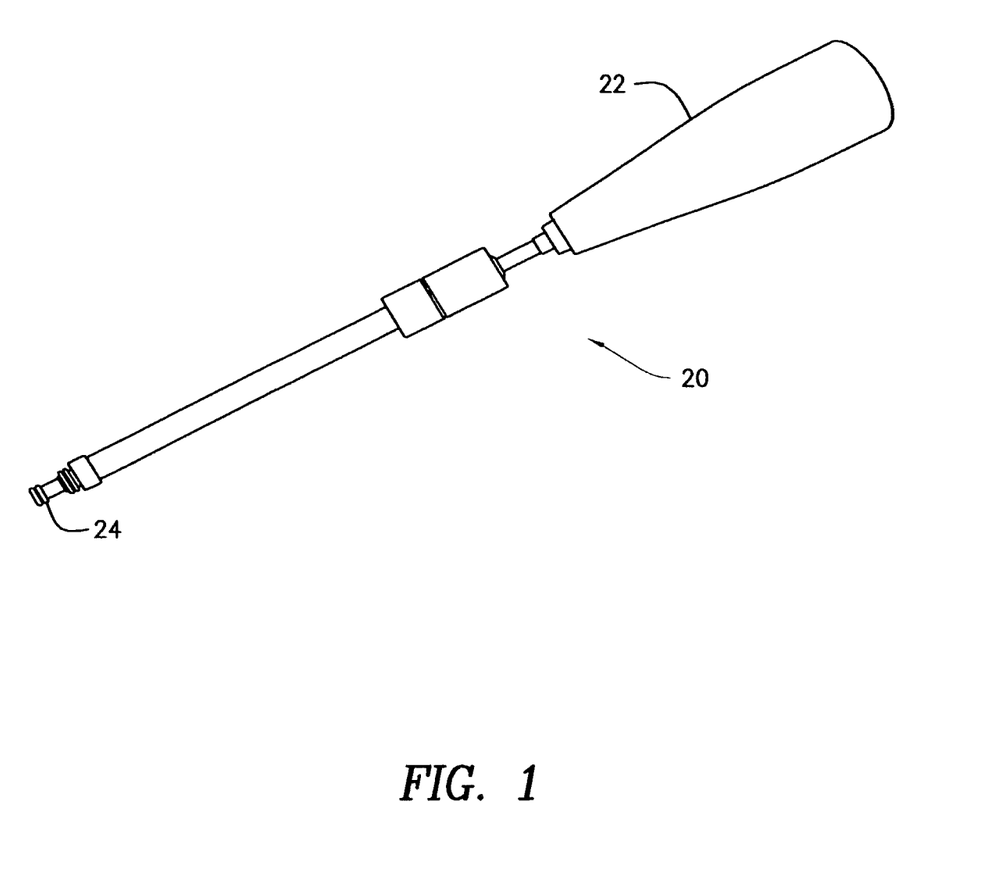
FIG. 1 is a color perspective view of a polyaxial screwdriver.

FIG. 1 shows a polyaxial screwdriver 20. The polyaxial screwdriver 20 has a handle 22 and a screw engaging end 24. The screw engaging end 24 engages the head of a polyaxial screw such that when the screwdriver 20 is rotated via the handle 22, the polyaxial screw is advanced or retracted in the vertebra. The polyaxial screwdriver 20 has an internal shaft 21 (FIG. 2A) that connects to the handle 22 and has a screw engaging end 24 (FIG. 3) formed on the end opposite the handle 22. An outside sleeve 23 is slidably inserted over the internal shaft 21.

Figure 3:
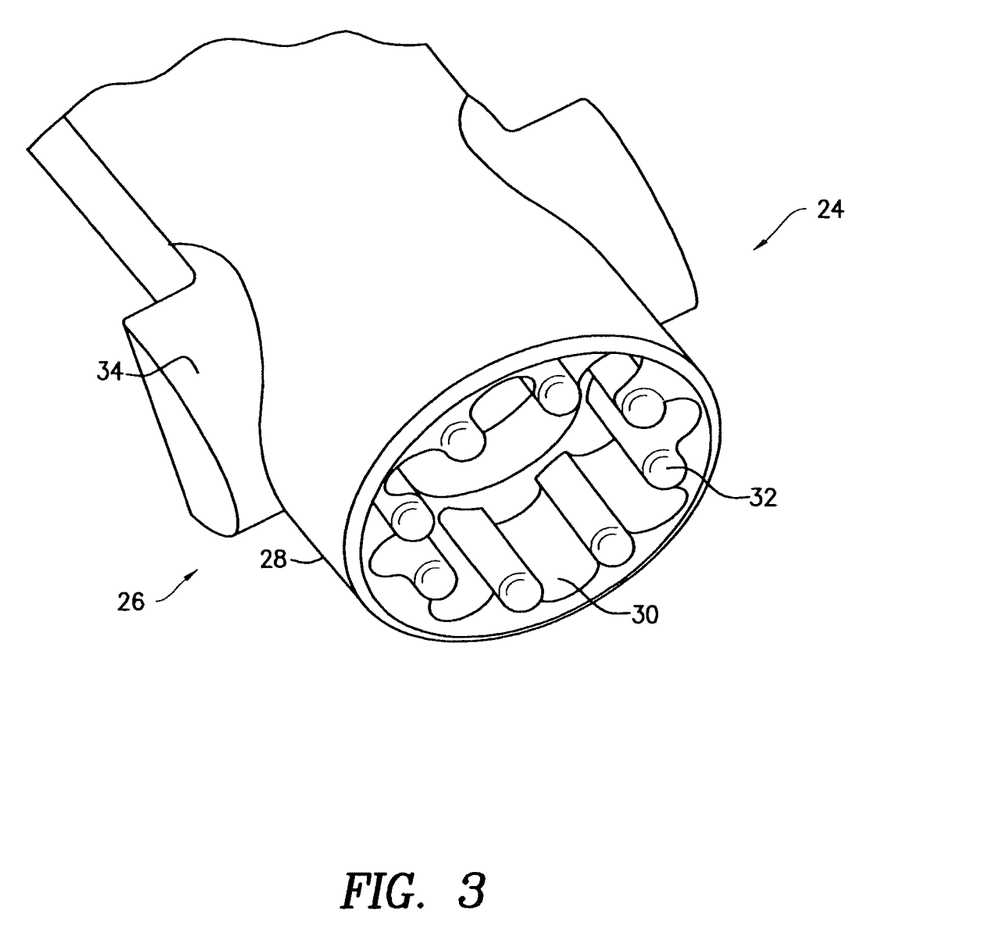
FIG. 3 is a color perspective view of the screw engaging end of the polyaxial screwdriver of FIG. 2.

The screw engaging end 24 has a hollow cylindrical portion 26. The hollow cylindrical portion 26 has a cylindrical external surface 28. The internal surface of the hollow cylindrical portion 26 has semi-cylindrical cutouts 30 that are spaced at a distance from each other. Placed between the semi-cylindrical cutouts 30 are cylindrical structures 32. The cylindrical structures 32 project beyond the edge of the semi-cylindrical cutouts 30 and towards the center of the hollow cylindrical portion 26. Thus, the semi-cylindrical cutouts 30 and the cylindrical structures 32 alternate around the internal periphery of the cylindrical end 26. There may be, for example, eight semi-cylindrical cutouts 30 and eight cylindrical structures 32. Any appropriate number of the semi-cylindrical cutouts 30 and the cylindrical structures 32 may be used. For example, there could be between two and twenty of each of the semi-cylindrical cutouts 30 and the cylindrical structures 32. In alternative embodiments, the cutouts can be of spherical, conical, rectilinear or any other suitable shape. Similarly, the cylindrical structures 32 can alternatively be of spherical, conical, rectilinear or any other suitable shape. The external surface of the screw engaging end 24 has two lateral projections 34 located diametrically opposite each other. Alternative embodiments may not include the two lateral projections 34.

Figure 4:
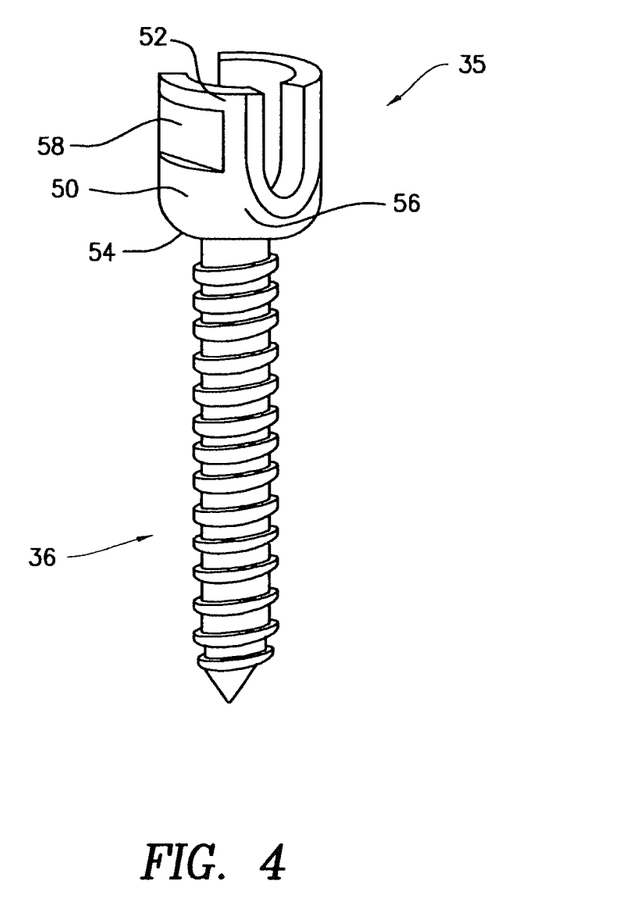
FIG. 4 is a color perspective view of a polyaxial bone screw assembly.
Figure 5:
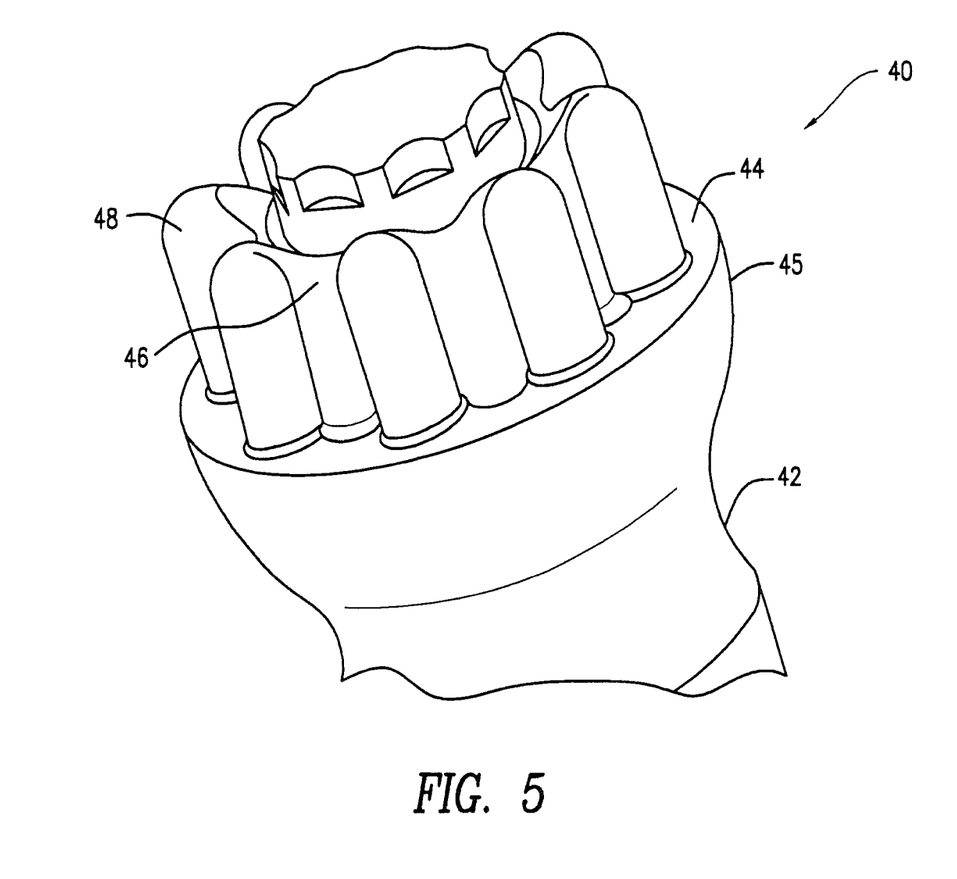
FIG. 5 is a color perspective view of the head portion of the polyaxial bone screw of FIG. 4.

FIG. 4 shows a polyaxial bone screw assembly 35 having a bone screw 36. The polyaxial bone screw 36 has threads 38 and a head 40 (FIG. 5). The threads 38 terminate at a neck 42 located between the threads 38 and the head 40. The neck 42 has a concave surface having a diameter that is less than the diameter of the threads 38. The reduced diameter neck 42 allows the screw 36 to pivot and rotate through a broader range of motion. The screw, including the external threads 38, neck 42 and head 40, is preferably made of a non-organic material that is durable and that can be implanted in a human body, such as titanium or stainless steel. Commonly assigned U.S. Pat. Nos. 6,488,681, and 6,554,834, the disclosures of which are incorporated by reference herein, disclose polyaxial bone screw of various designs. Any of the bone screws described in the '681 patent or the '834 patent may be adapted for use with the screwdriver of the present invention that has been appropriately modified.

Figure 6:
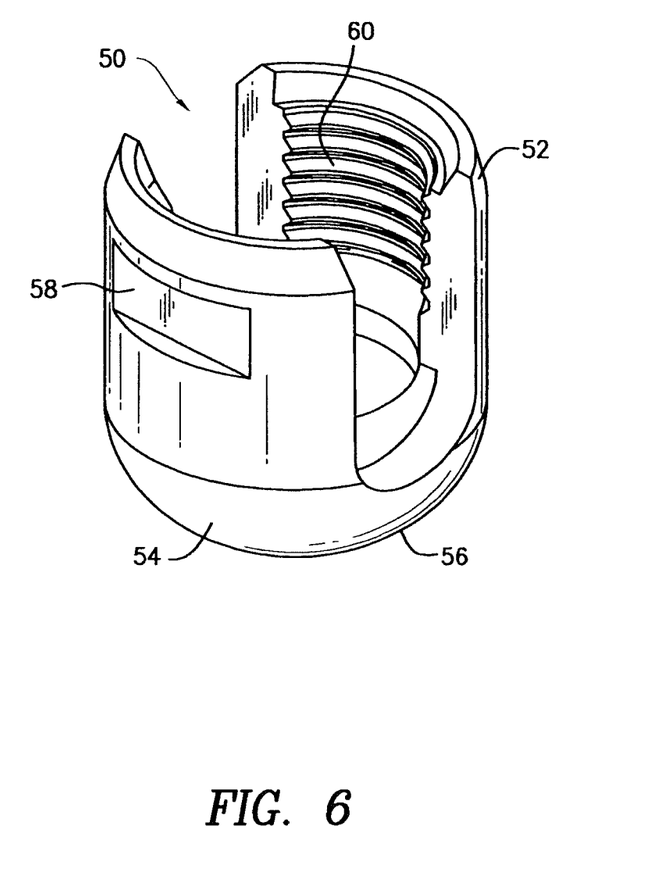
FIG. 6 is a perspective view of a coupling element used with the polyaxial bone screw assembly of FIG. 4.

Polyaxial bone screw assembly 35 also includes a coupling element 50 (also known as a tulip; FIG. 6) for coupling an orthopedic stabilizing rod with the polyaxial screw assembly 35. Coupling element 50 is preferably made of an inert material such as titanium or stainless steel. Coupling element 50 has an upper end 52 and a lower end 54. Coupling element 50 also preferably has an outer surface 56 including a convex surface at the lower end 54 thereof and a cylindrical surface at the upper end thereof. Outer surface 56 also preferably includes one or more grooves 58 formed therein so that coupling element 50 may be grasped using a tool.

The coupling element 50 has a bore for receiving the screw 36. The bore defines an inner surface of coupling element 50 and has internal threads 60 at the inner surface of the upper end 52 of the coupling element 50. The lower end of the bore preferably has a shape adapted to accommodate head 40. In other embodiments, the threads on the coupling element may be external threads. The head 40 of the screw 36 sits at the bottom of the coupling element 50.

The head 40 includes a flat surface 44. The head 40 has a spherical surface 45 that is located below the flat surface 44. A cylindrical wall 46 is formed on the flat surface 44. Solid cylinders 48 are formed on the outside surface of the cylindrical wall 46. The solid cylinders 48 are equidistant from their neighboring solid cylinders 48. The solid cylinders 48 are located on the head 40 such that they can align with the semi-cylindrical cutouts 30 when the screw engaging end 24 is placed on top of the head 40. The solid cylinders are sized so that they will slide snugly in the semi-cylindrical cutouts 30 when the screw engaging end 24 is lowered on the head 40. Additionally, when the screw engaging end 24 is lowered on the head 40, the cylindrical structures 32 slide in the region between the solid cylinders 48. When the screw engaging end 24 is lowered on the head 40, it is possible that there is slight misalignment between the solid cylinders 48 and the semi-cylindrical cutouts 30. However, when such misalignment exists, the edges of the semi-cylindrical cutouts 30 will touch the top of the solid cylinders 48. Since the top of the solid cylinders 48 are sloping down the semi-cylindrical cutouts would slide on top of the solid cylinders 48 and thereby self-align. As is clear from the above description, the shape and size of the solid cylinders 48 and cylindrical wall 46 are complimentary to the shape and size of the semi-cylindrical cutouts 30 and cylindrical structures 32, respectively. Thus, in an alternative embodiment, for example, in an embodiment where the cutouts are made spherical, the solid cylinders 48 will also be replaced by spherical structures that are complimentary with the shape and size of the spherical cutouts. As discussed previously, shapes other than the spherical may also be used.

Figure 7:
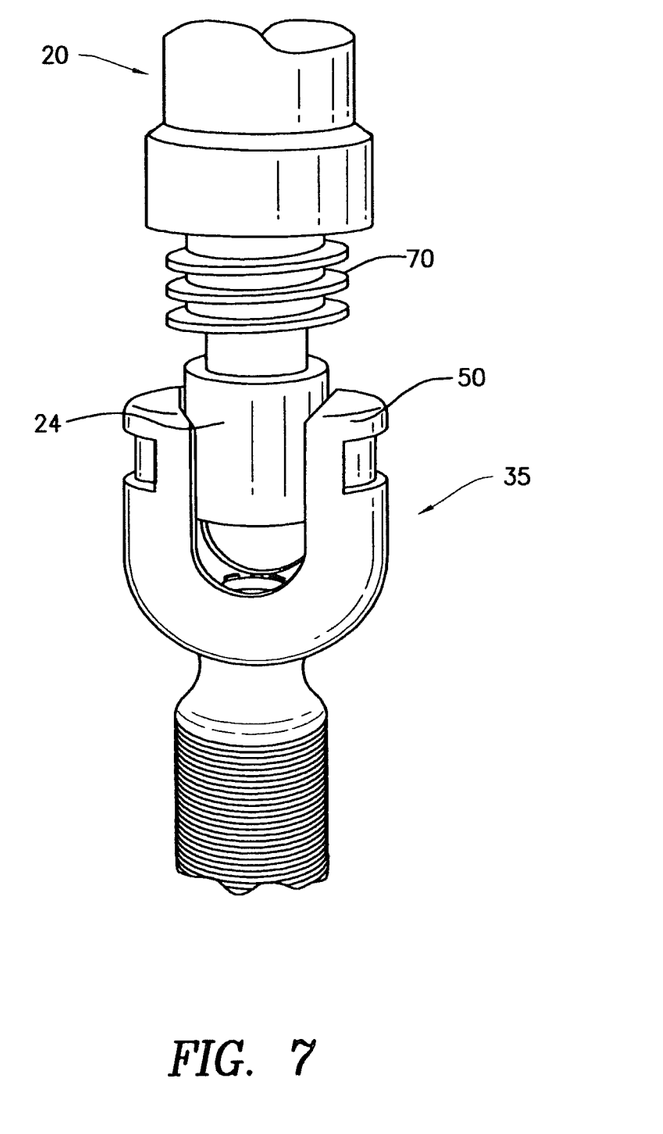
FIG. 7 is a perspective view of polyaxial screwdriver inserted in the polyaxial bone screw assembly of FIG. 4.

FIG. 7 shows the screwdriver 20 being inserted in the polyaxial bone screw assembly 35. The screw engaging end 24 is shown inserted in the coupling element 50. As the screw engaging end 24 is lowered further in the coupling element 50, threads 70 would align with threads 60 (FIG. 6). Rotation of handle 22 would rotate shaft 21 along with threads 70. Such rotation, when the screw engaging end 24 is engaged with the screw head 40, results in advancing the screw 36 in the bone and engaging together threads 70 and 60. The precise mating of the screw engaging end 24 and head 40 along with the engagement of threads 60 and 70 results in secure attachment of the screwdriver to the screw.

Figures 2, 2A:
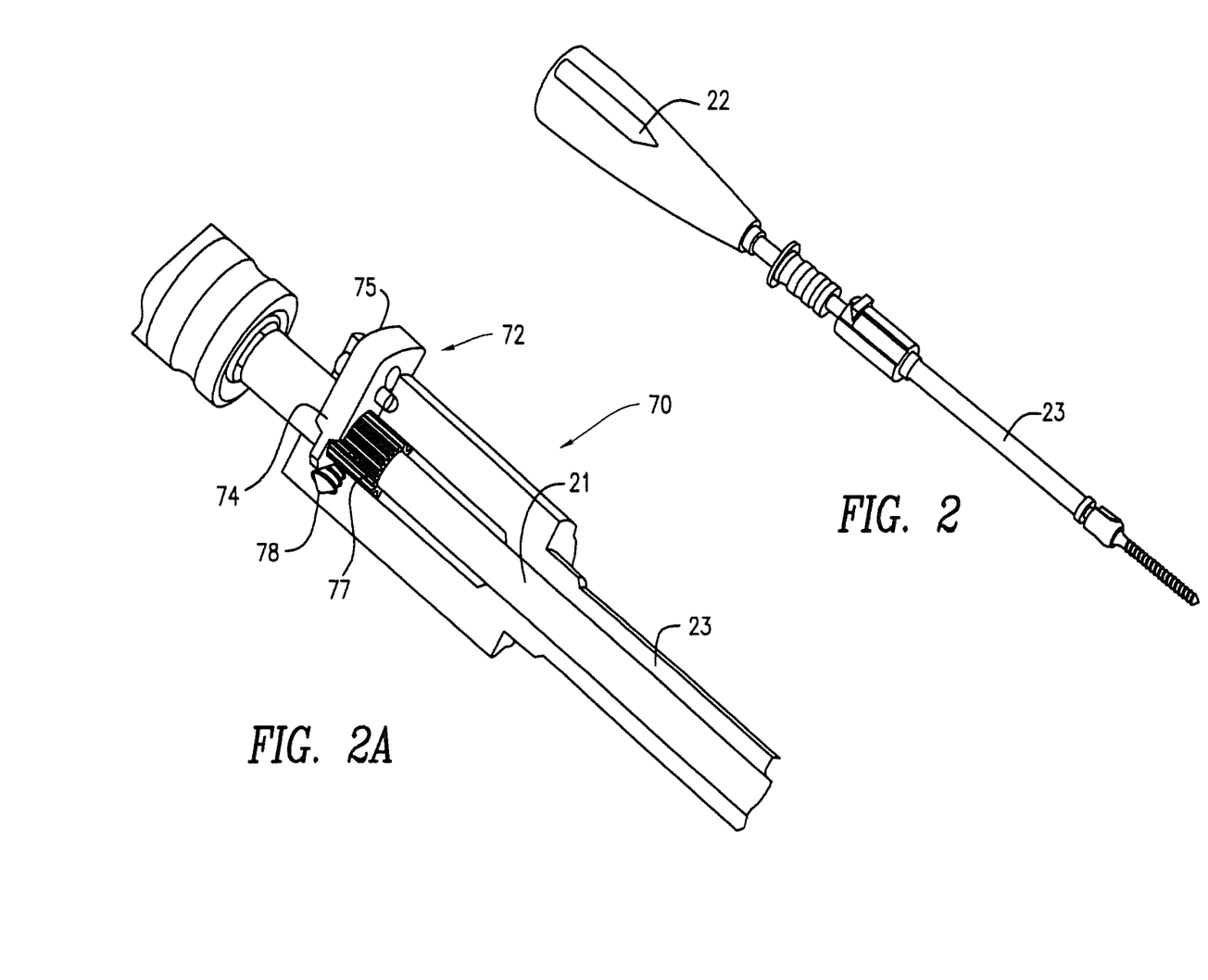
FIG. 2 is a color perspective view of another embodiment of a polyaxial screwdriver.
FIG. 2A is a color cross-sectional perspective view of the polyaxial screwdriver of FIG. 2.

FIG. 2A shows an improved locking mechanism 72. The locking mechanism 72 includes a ratchet 74 that is attached to the sleeve 23 via a key 76 that is inserted in the sleeve 23 and the ratchet 74. The ratchet 74 has a button 75 that is integral with ratchet 74 and projects from the surface of the sleeve 23. The ratchet 74 is in engagement with gear teeth 77 formed on the outside of internal shaft 21 in the region corresponding to the location of the ratchet 74. A spring 78 applies a force to the ratchet to keep it in engagement with the gear teeth 77. Therefore, in use, when the handle 22 is rotated to insert the screw 36 in a vertebra the threads 60 and 70 engage each other and at the same time the ratchet 74 is progressively engaged with the gear teeth 77. This results in progressive and automatic locking of the polyaxial screwdriver and prevents the accidental unthreading from the coupling element 50 and loosening of the screwdriver. When the screwdriver is used to unthread the screw 36, the button 75 is pressed to disengage the ratchet 74 from the gear teeth 77 and thereby allow the internal shaft 21 to be rotated in reverse direction to unthread screw 36.

Figures 8, 9:
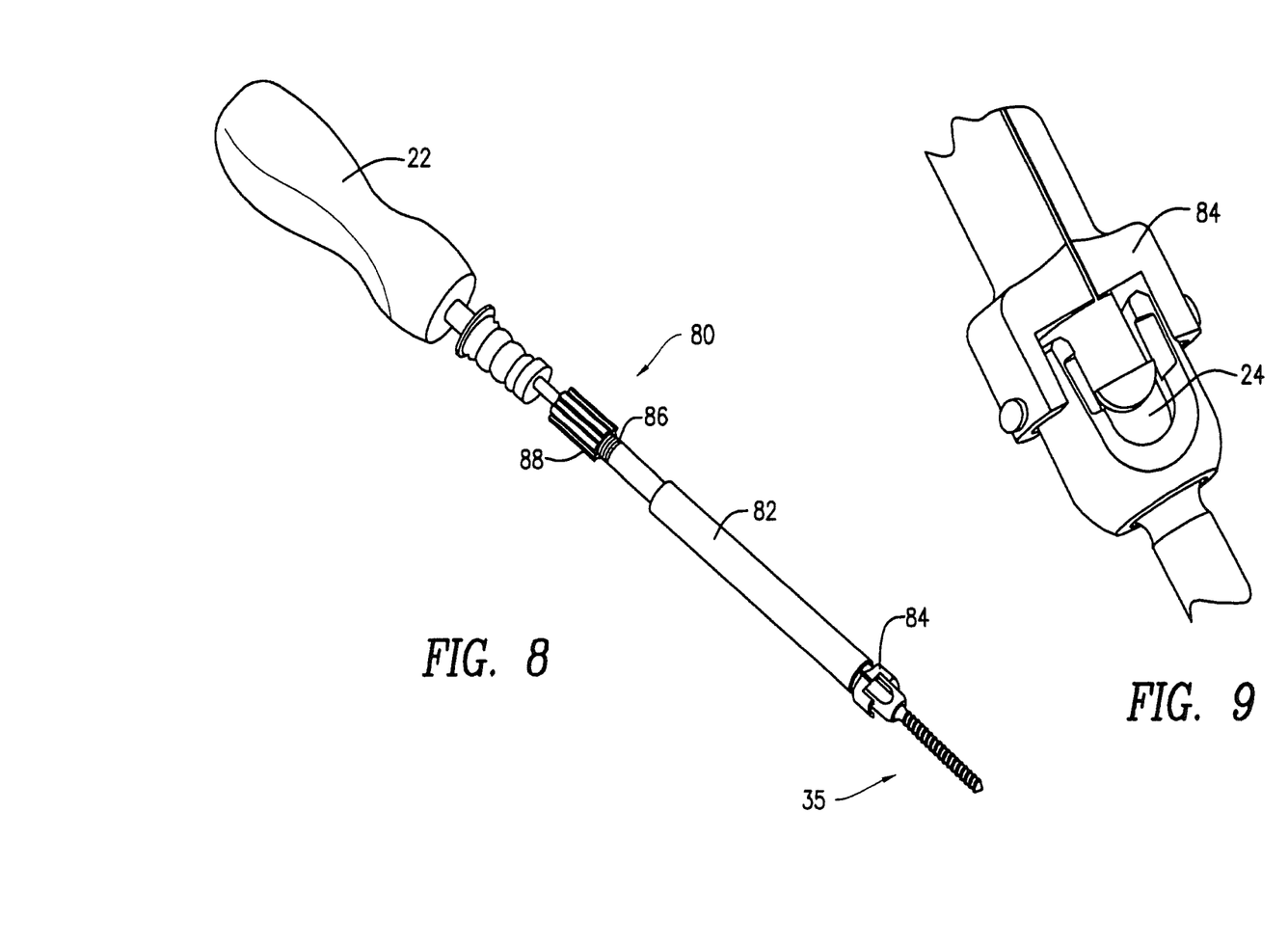
FIG. 8 is a color perspective view of another embodiment of polyaxial screwdriver engaged with the polyaxial bone screw assembly of FIG. 4.
FIG. 9 is a color enlarged view of the collet section of the polyaxial screwdriver of FIG. 8.

FIGS. 8-9 show another embodiment of a polyaxial screwdriver 80 engaged with the polyaxial bone screw assembly 35. The construction of the polyaxial screwdriver 80 is similar to the polyaxial screwdriver 20 in many respects. Therefore, only the features of the polyaxial screwdriver 80 that are different from the polyaxial screwdriver 20 are described hereafter. Same reference numeral denotes parts that are similar across various embodiments. The outer sleeve 82 of the polyaxial screwdriver 80 has a collet 84 formed at the end that is near the screw engaging end 24. Projections (not seen in figures) are formed on the internal surface of the collet 84. The end of the sleeve 82 that is closer to the handle 22 has external threads 86 formed on it. A nut 88 is next to the threads 86. The nut 88 has internal threads that are adapted to threadably engage threads 86. The nut 88 is in contact with a shoulder formed on shaft 21 such that it is prevented from sliding towards the collet 84. When the polyaxial screwdriver is lowered on the head 40 collet 84 slides over the outside surface of the upper end 52 of the coupling element 50. The projections on the internal surface of the collet 84 snap in the grooves 58 formed on the outer surface 56 of the coupling element 50. Once the polyaxial screwdriver 80 is in engagement with screw 36, and the collet is in place around the coupling element 50 the nut 88 is threaded on to the threads 86 to securely fasten the screwdriver 80 to the polyaxial bone screw assembly 35. Since the nut 88 cannot slide towards the collet 84, when the nut 88 is threaded on the sleeve 82, sleeve 82 is pulled up towards the handle 22 to securely fasten the screwdriver 80 to the polyaxial bone screw assembly 35. The engagement of the screw engaging end 24 of polyaxial screwdriver 80 to the head of the screw 36 is same as described previously.

Figures 10, 11:
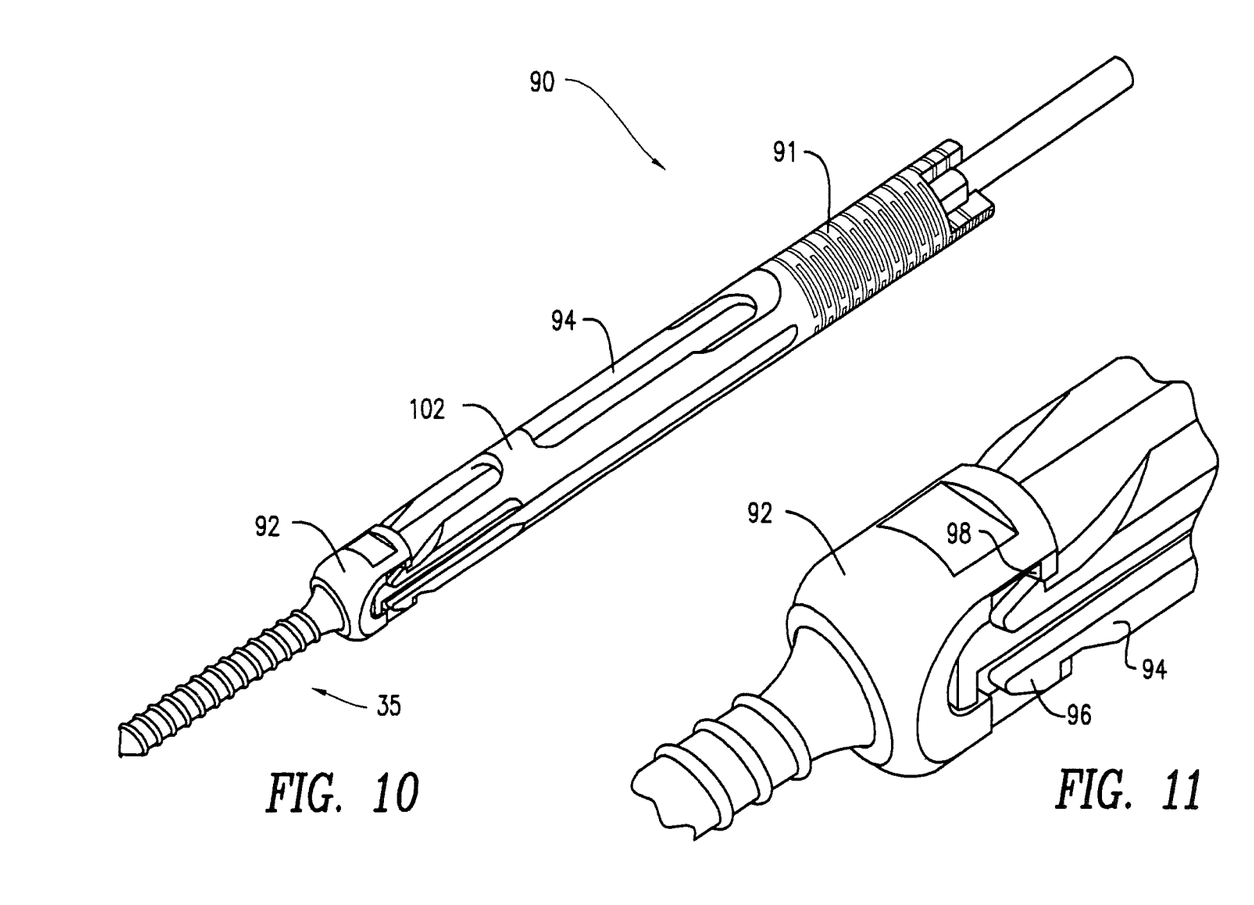
FIG. 10 is a color perspective view of another embodiment of polyaxial screwdriver engaged with the polyaxial bone screw assembly of FIG. 4.
FIG. 11 is a color enlarged view of the section of the polyaxial screwdriver of FIG. 10 that is engaged with the polyaxial bone screw assembly.
Figure 12:
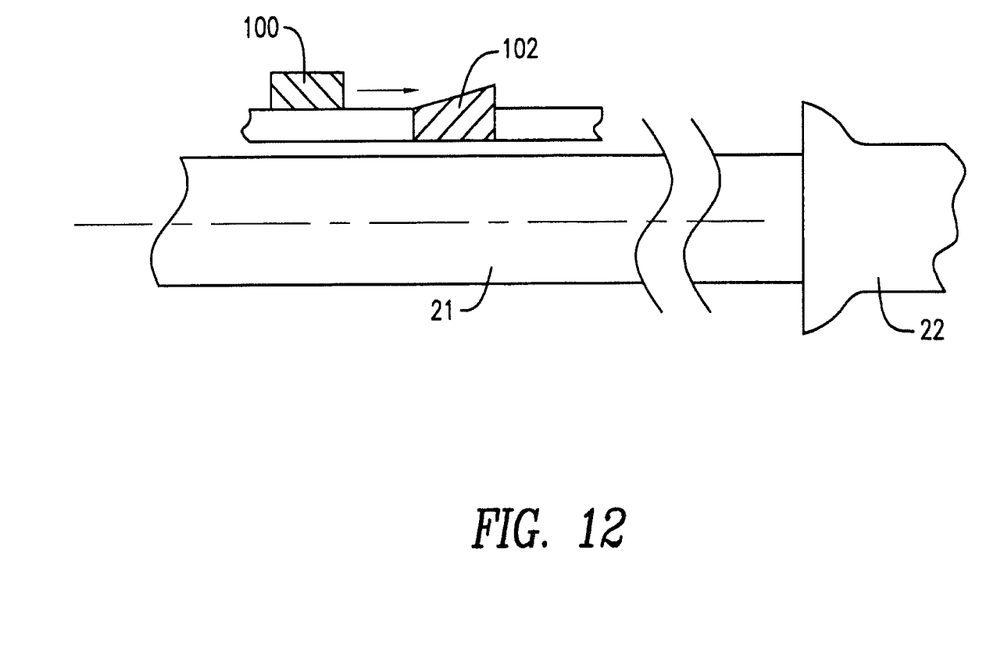
FIG. 12 is a partial cross-sectional view of the polyaxial screwdriver of FIG. 10 showing a ramp formed on the sleeve and a ring mounted on the sleeve.

FIGS. 10-11 show yet another embodiment of a polyaxial screwdriver 90 engaged with the polyaxial bone screw assembly 35. The construction of the polyaxial screwdriver 90 is similar to the polyaxial screwdriver 20 in many respects. Therefore, only the features of the polyaxial screwdriver 90 that are different from the polyaxial screwdriver 20 are described hereafter. Same reference numeral denotes parts that are similar across various embodiments. The outer sleeve 91 of the polyaxial screwdriver 90 has a split end. The end that engages the coupling element 92 is split to form two flexible arms 94. The ends of the flexible arms 94 that engages the coupling element 92 have a step 96 formed thereon. Steps 98 of complimentary shape are formed on the internal surface of the coupling element 92. The steps 98 replace the internal threads of the embodiment of FIG. 6. An internal spring (not seen in the FIGS. 10-11) pulls the sleeve 91 tight with respect to the polyaxial bone screw assembly 35 thereby keeping the flexible arms 94 engaged with the coupling element 92. A short ring (FIG. 12) 100 is located around the outer sleeve 91. The short ring 100 when pulled towards the handle 22 would engage ramps 102 formed on the external surfaces of the arms 94 thereby deflecting arms 91 towards the center of the sleeve 91 and allowing them to disengage from the coupling element 92.

In use the polyaxial screwdriver of any one of the above described embodiment is lowered on the polyaxial bone screw assembly 35. When the screw engaging end 24 contacts the head 40 of the screw 36, and the screwdriver is lowered further the relative position of the engagement features on the screw engaging end 24 and the head 40 are automatically adjusted to allow smooth engagement of the screw engaging end 24 with the head 40. Additionally, the engagement between the screw engaging end 24 and the head 40 is made secure by any one of the various methods described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of affixing a pedicle screw to a vertebra, comprising:
    coupling a screw engaging end of a shaft of a screwdriver with a head of a pedicle screw;
    advancing threads positioned at a distal end of a sleeve of the screwdriver into threaded engagement with a threaded portion of a coupling element coupled to the pedicle screw, the sleeve being disposed coaxially around the shaft of the screwdriver;
    activating a locking mechanism directly connected to the sleeve so as to prevent the threads of the screwdriver from disengaging the threaded portion of the coupling element.

2. The method of claim 1, wherein the locking mechanism is configured such that the activating of the locking mechanism occurs automatically when performing the step of advancing the threads into threaded engagement with the threaded portion of the coupling element.

3. The method of claim 1, wherein the advancing of the threads into threaded engagement with the threaded portion of the coupling element includes rotating the threads in a first direction about a longitudinal axis of the screwdriver, and wherein the activating of the locking mechanism prevents rotation of the threads in a second direction opposite to the first direction.

4. The method of claim 1, further comprising rotating the shaft of the screwdriver to advance the pedicle screw into vertebral bone.

5. The method of claim 1, further comprising deactivating the locking mechanism.

6. The method of claim 5, wherein the deactivating of the locking mechanism includes depressing a button positioned on the sleeve.

7. The method of claim 6, wherein the button is biased to maintain the locking mechanism in a state of being activated.

8. The method of claim 5, further comprising disengaging the threads from the threaded portion of the coupling element.

9. A method of affixing a pedicle screw to a vertebra, comprising:
   engaging a screw engagement interface of a screw engaging end of a screwdriver with a complementary driver engagement interface of a head of a pedicle screw such that the screw engagement interface and the driver engagement interface move into a first one of a plurality of discrete possible engaged positions, the screw engagement interface and the driver engagement interface being configured to mate with one another in each of the plurality of discrete possible engaged positions, and each one of the plurality of discrete possible engaged positions being defined by a different respective rotational alignment of the screw engagement interface relative to the driver engagement interface about a longitudinal axis of the pedicle screw, the pedicle screw having an elongated threaded portion extending distally from the head along the longitudinal axis, wherein the screw engagement interface and the driver engagement interface are configured such that a rotational misalignment between the screw engagement interface and the driver engagement interface about the longitudinal axis during the engaging step causes the screw engagement interface and the driver engagement interface to rotate relative to one another about the longitudinal axis until the screw engagement interface and the driver engagement interface move into one of the plurality of discrete possible engaged positions; and
   while the screw engagement interface and the driver engagement interface are in the first one of the discrete possible engaged positions, rotating the screwdriver to advance the elongated threaded portion of the pedicle screw into vertebral bone.

10. The method of claim 9, wherein the driver engagement interface of the head of the pedicle screw includes a plurality of sloping features spaced apart circumferentially around the longitudinal axis, each one of the plurality of sloping features having a first sloping portion sloping in a first circumferential direction with respect to the longitudinal axis and a second sloping portion sloping in a second circumferential direction with respect to the longitudinal axis, the second circumferential direction being opposite to the first circumferential direction.

11. The method of claim 10, wherein the driver engagement interface includes a plurality of recessed regions spaced apart circumferentially around the longitudinal axis, each of the plurality of recessed regions being defined between adjacent ones of the plurality of sloping features, and wherein the plurality of recessed regions are each configured to matingly receive a respective complementary protruding feature of the screw engagement interface of the screwdriver in each of the plurality of discrete possible engaged positions.

12. The method of claim 10, wherein the screw engagement interface and the driver engagement interface are configured such that, for any rotational misalignment between the screw engagement interface and the driver engagement interface about the longitudinal axis during the engaging step, the plurality of sloping features cause the screw engagement interface and the driver engagement interface to rotate relative to one another in whichever one of the first and second circumferential directions about the longitudinal axis involves a shorter magnitude of angular rotation until the screw engagement interface and the driver engagement interface move into one of the plurality of discrete possible engaged positions.

13. The method of claim 10, wherein each of the sloping features is dome shaped.

14. The method of claim 9, wherein the driver engagement interface of the head of the pedicle screw includes a central projection, and wherein the screw engagement interface and the driver engagement interface are configured such that the rotational misalignment during the engaging step causes the screw engagement interface and the driver engagement interface to rotate relative to one another about the central projection.

15. The method of claim 14, wherein the central projection extends further proximally along the longitudinal axis than any other portion of the driver engagement interface.

16. The method of claim 9, wherein the pedicle screw includes a coupling element coupled to the head, the coupling element adapted to receive a stabilizing rod therein.

17. The method of claim 16, wherein the coupling element is coupled to the head of the pedicle screw such that the coupling element is pivotable relative to the elongated threaded portion.

18. The method of claim 17, wherein the coupling element is polyaxially coupled to the head of the pedicle screw such that the coupling element can pivot relative to the elongated threaded portion about a plurality of axes.

19. The method of claim 15, further comprising advancing threads positioned at a distal end of a sleeve of the screwdriver into threaded engagement with a threaded portion of the coupling element.

20. The method of claim 19, further comprising activating a locking mechanism directly connected to the sleeve so as to prevent the threads of the screwdriver from disengaging from the threaded portion of the coupling element.

* * * * *